CHRYSANTHEMUM PLANT
Filed Nov. 27, 1973
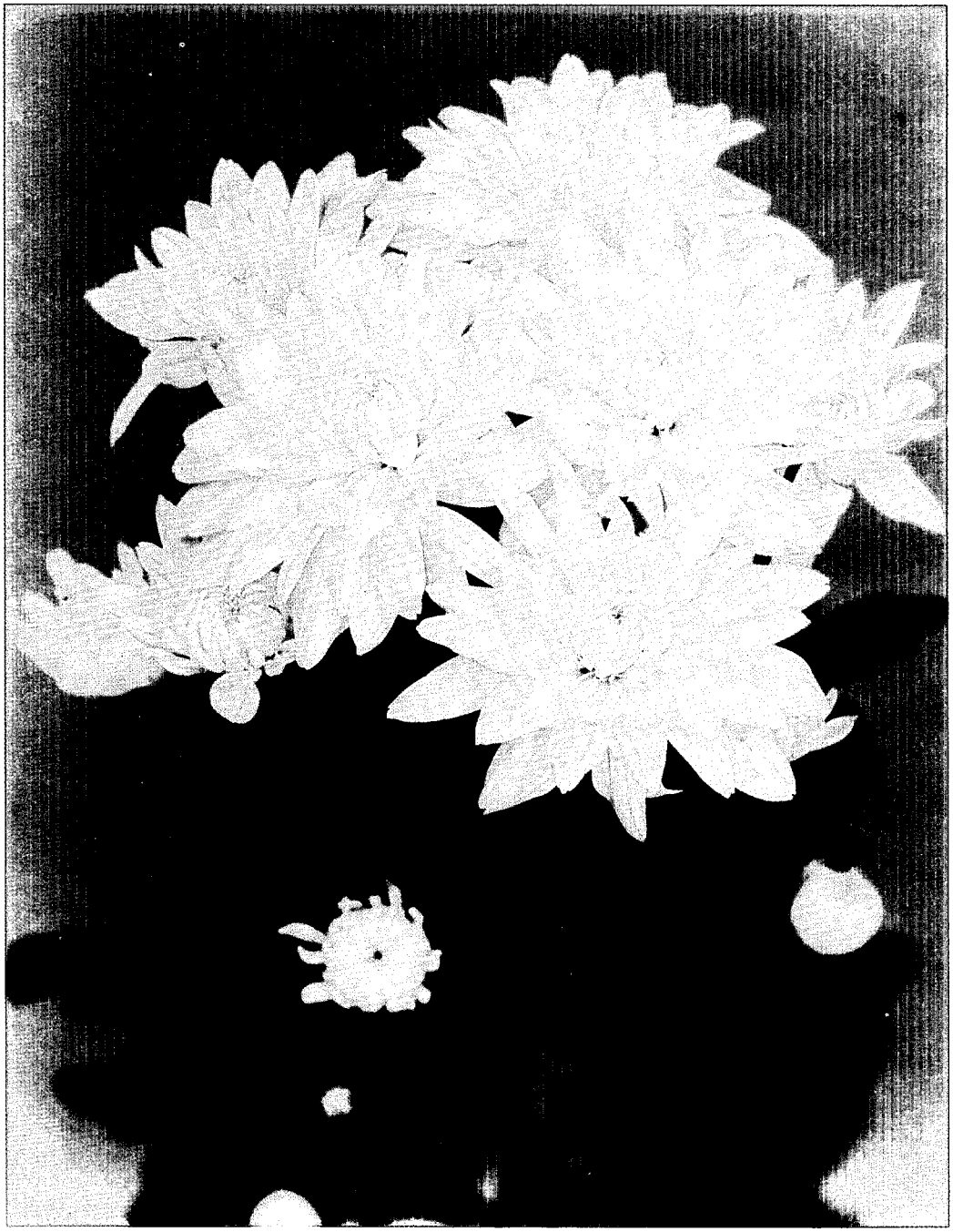

United States Patent Office

Plant Pat. 3,673
Patented Dec. 24, 1974

3,673
CHRYSANTHEMUM PLANT

Walter H. Jessel, Jr., Doylestown, and William E. Duffett, Akron, Ohio, assignors to Yoder Brothers, Inc., Barberton, Ohio

Filed Nov. 27, 1973, Ser. No. 419,271
Int. Cl. A01h *5/00*
U.S. Cl. Plt.—78 1 Claim

The present invention comprises a new and distinct cultivar of chrysanthemum plant known by the varietal name Solarama which is a seedling of the cultivar Arctic, disclosed in U.S. Plant Pat. 3,326, issued May 8, 1973, × the cultivar Polaris, an unpatented but well known commercial variety.

The new cultivar is similar in many respects to the cultivar Yellow Show-Off, which is disclosed in U.S. Plant Pat. 3,334, issued May 15, 1973. The new cultivar has the same characteristics as Yellow Show-Off of:

1. Use as a yellow decorative for cut spray programs.
2. Tolerance of 48° F. temperatures for uniform bud initiation and development.
3. Tolerance of marginally high temperatures (75° F.) for uniform bud initiation and development.

The new cultivar is distinguished from Yellow Show-Off by the following characteristics, when grown under comparable conditions:

1. No non-breaking tendencies from a pinch at marginally high temperatures (above 70° F.).
2. Approximately ½" larger flower size.
3. Improved color retention and less reflexing of form resulting in 4–6 days longer bench life and durability under average home conditions.
4. A darker yellow flower color.
5. Reduced tendency to show open centers in early spring and late fall flowerings.
6. 2"–3" less vigor.
7. Three to five days earlier response.

The new cultivar was selected from the progeny of the designated cross, and when asexually reproduced by cuttings at Barberton, Ohio, has been found to retain its distinctive characteristics through successive propagations.

The new cultivar when grown in the vicinity of Barberton, Ohio, has a response period of approximately 8 weeks, and the following detailed description is based on observations made of the new cultivar in a greenhouse at Barberton, Ohio, grown at a minimum of 60° F. night temperatures. The response time, blooming period, color, and total vigor may vary significantly with varying environmental conditions such as temperature, daylength, and light intensity. Suggested flowering for 60° F. night temperature programs in the northern United States is from May through October; southeastern United States, southwestern United States, and coastal California, April through November; for southern Florida under outdoor conditions where less than 60° F. night temperatures may not be provided, and southern California in low temperature poly houses where night temperatures are normally less than 56° F., November through April.

The accompanying drawing shows the unique characteristics of the new cultivar, the color being as nearly true as possible with color illustrations of this type.

In the description which follows, color references are made to the Munsell Color Book, 1963 edition (MBC), Munsell Limit Color Cascade, 1972 edition (MLCC), and comparisons are made with the cultivar Yellow Show-Off. Where only a single value or description appears for the new cultivar, the same value or description applies as well to the comparison cultivar.

Botanical classification: *Chrysanthemum morifolium*, Ramat

| | Solarama | Yellow Show-Off |
|---|---|---|
| Bloom: | | |
| *Size* | 3"–3¼" | 2½"–2¾". |
| *Fully expanded* | 3½" | 3". |
| *Borne* | Clusters on elongated pedicels. | |
| *Stems* | Strong | |
| *Form* | Decorative | |
| *Permanence* | 14–18 days | 10–12 days. |
| *Color:* | | |
| Center of flower | Dark yellow, 5Y8.5/14 (MBC). | Yellow-green, 10Y7/10 (MBC). |
| Base of petals | Yellow-green, 2.5-GY7/10 (MBC). | Yellow-green, 2.5-GY7/10 (MBC). |
| Inside of petals | Dark yellow, 5Y8.5/14 to yellow, 3.0Y-8.5/7.7 (MLCC). | Yellow, 7.5Y8.5/12 to yellow, 3.0Y8.5/7.7 (MLCC). |
| Reverse of petals. | Yellow, 3.0Y8.5/7.7 (MLCC). | Light yellow, 7.5Y9/6 (MBC). |
| Tonality from a distance. | Dark yellow | Yellow. |
| Discoloration | Yellow, 3.0Y8.5/7.7 (MLCC). | Yellow, 3.0Y8.5/7.7 (MLCC). |
| Petals: | | |
| *Texture* | Smooth | |
| *Appearance and form.* | Open at base, wide multi-furrowed keel tapering to a blunt tip with occasional reverse roll of petal edges. | Open at base, smooth flat keel, tapering to a blunt tip. |
| *Arrangement* | Composite, whorled on a single receptacle. | |
| *Persistence* | Resists shatter | |
| *Fragrance* | Typical chrysanthemum. | |
| Reproductive organs: | | |
| *Stamen, anthers* | 10–15 | None to 35. |
| *Pollen* | Scant | None to scant. |
| *Arrangement* | Clustered in center of flower, if present. | |
| *Styles* | Present both ray and disc florets. | |
| *Length* | Short | |
| *Ovaries* | At the base of petal attached to receptacle. | |
| Plant: | | |
| *Form* | Herbaceous | |
| *Growth* | Upright | |
| *Height* | Approximately 32"–34" given 2–3 long day weeks and a total crop time of 10–11 weeks for programs with 60° F. night temperatures as defined in the timetables of Yoder Brothers, Inc., Barberton, Ohio, for the various seasons. | Approximately 34"–36" given 2–3 long day weeks and a total crop time of 11–12 weeks for programs with 60° F. night temperatures as defined in the timetables of Yoder Brothers, Inc., Barberton, Ohio, for the various seasons. |
| *Spread* | None grown single stem to slight when grown pinched. | |
| Foliage: | | |
| *Top side* | Dark green, 7.5GY3/4 (MBC). | |
| *Size* | Length to width ratio 20:11 with length to 5" and width to 2¾". | Length to width ratio 13:6 with length to 6½" and width to 3". |
| *Quantity* | Numerous | |
| *Shape* | Spatulate lobed | |
| *Texture* | Smooth | |
| *Ribs and veins* | Prominent | |
| *Edge* | Deeply indented | |
| *Serration* | Moderate | |
| *Under side* | Greyed green, 7.5GY5/4 (MBC). | |
| *Stipules* | Prominent | Rudimentary to prominent. |

We claim:

1. A new and distinct cultivar of chrysanthemum characterized particularly as to its uniqueness when compared to the cultivar Yellow Show-Off by its lack of non-breaking tendencies from a pinch at marginally high temperatures (above 70° F.); approximately ½″ larger flower size; improved color retention and less reflexing of form resulting in 4–6 days longer bench life and durability under average home conditions; a darker yellow flower color; reduced tendency to show open centers in early spring and late fall flowerings; 2″–3″ less vigor, and by its three to five days earlier response.

No references cited.

ROBERT E. BAGWILL, Primary Examiner